United States Patent [19]

Boehm et al.

[11] Patent Number: 4,631,688
[45] Date of Patent: Dec. 23, 1986

[54] METHOD OF AND APPARATUS FOR TESTING A METAL BODY BY MEANS OF EDDY CURRENTS

[76] Inventors: Bernard Boehm, 35, rue de la Croix de Fer, 78100 Saint-Germain-en-Laye; Marc Lacroix, 6, Impasse des Pêcheries, 78230 Le Pecq, both of France

[21] Appl. No.: 157,632

[22] Filed: Jun. 6, 1980

[30] Foreign Application Priority Data

Jun. 14, 1979 [FR] France .................................. 79 15481

[51] Int. Cl.⁴ ...................... G06F 15/20; G01R 33/12
[52] U.S. Cl. .................................... 364/507; 324/216; 324/233; 364/481
[58] Field of Search ................................ 364/480–483, 364/507, 552; 324/216, 222, 228, 233, 237, 238

[56] References Cited

U.S. PATENT DOCUMENTS

| | | | |
|---|---|---|---|
| 3,295,362 | 1/1967 | Wood et al. ........................ | 364/507 |
| 3,422,346 | 1/1969 | Hammer .............................. | 324/233 |
| 3,697,868 | 10/1972 | Carossi et al. ..................... | 324/237 |
| 4,107,605 | 8/1978 | Hudgell .............................. | 324/238 |
| 4,109,201 | 8/1978 | Pigeon et al. ....................... | 324/238 |
| 4,207,520 | 6/1980 | Flora et al. ......................... | 324/233 |
| 4,263,551 | 4/1981 | Gregory et al. .................... | 324/233 |
| 4,283,680 | 8/1981 | Kerr ................................... | 324/233 |

*Primary Examiner*—Errol A. Krass
*Attorney, Agent, or Firm*—Michael J. Striker

[57] ABSTRACT

A metal body is inspected for defects by relatively longitudinally displacing it and a plurality of pairs of coils connected in respective bridge circuits that are excited with alternating current. The coils are also excited with alternating current so that eddy-current variations caused by defects in the body become impedance variations of the coils which in turn become imbalance signals in the respective bridges. The imbalance signals are demodulated to form respective imbalance voltages which are periodically sampled and the levels of the sampled demodulated voltages are stored. The sampled demodulated voltages of each bridge are averaged to produce respective base lines which are compared with the respective stored levels of each sampled voltage for generation of respective error signals corresponding to the differences. These error signals are compared with a first relatively low threshold corresponding to the smallest defect to be detected and with a second relatively high threshold. When one of the error signals exceeds only the first threshold it indicates a small defect at the respective location on the body and when one of the error signals exceeds the second threshold it indicates a large defect. A longitudinal succession of at least abutting zones is established on the body and the error signals for each zone are summed. Each of these sums is compared with a predetermined third threshold and when one of the sums exceeds the third threshold it indicates a long defect in the respective zone.

10 Claims, 1 Drawing Figure

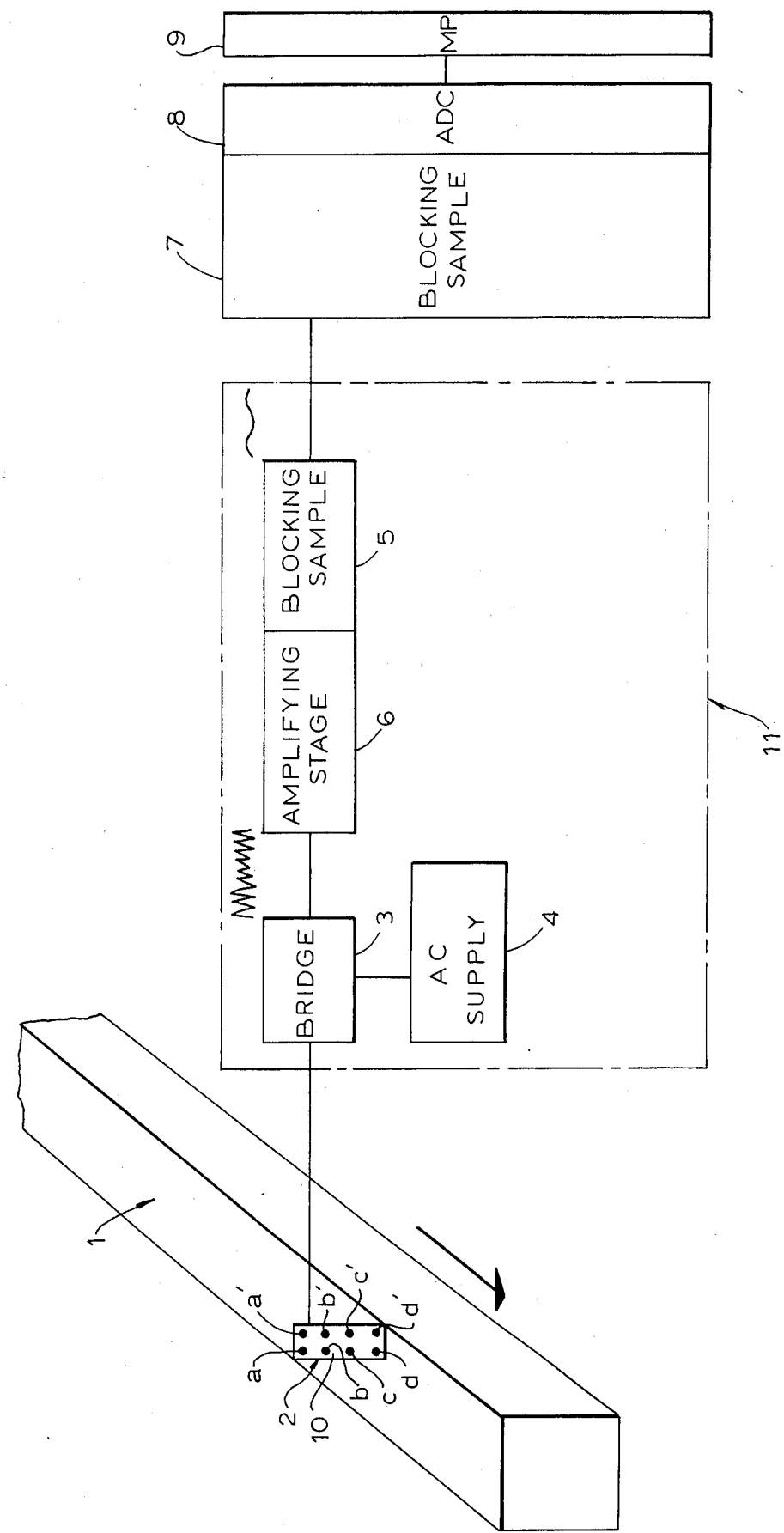

METHOD OF AND APPARATUS FOR TESTING A METAL BODY BY MEANS OF EDDY CURRENTS

TECHNICAL BACKGROUND OF THE INVENTION

The invention comes within the field of electromagnetic inspection of metal products by Foucault or eddy currents in order to detect surface defects.

A number of electromagnetic methods of probing surface defects are already known. They are largely based on a saturation magnetization of the product, the latter producing a gap in the magnetic field at the location of the defects as well as the appearance of leak lines. The heterogeneities of the field can then be materialized by sprinkling with iron filings, which accumulate at the defect locations. This method, designated by the term magnetoscopy, is quite sensitive, but does not yield good results on scaled products, furnishes no indication of the depth of the defects and is carried out almost whollymanually, especially in the locating of defects, which is visual. Optical detection is based on the same principle, but the use of a colored magnetic powder makes possible the observation of the product by means of a television camera and the locating of defects can be automated. The leakage flux method consists of measuring the magnetic field by use of Hall probes; it is hardly suitable for anything but scaled products, but, for the latter, it is relatively quantitative and makes it possible to estimate the extent of the defects; it can also be easily automated. The main disadvantages of all of these techniques are that they can be applied, under satisfactory sensitivity conditions, only to prescaled products and require premagnetization and then demagnetization of the product after probing. These two stages consume energy in quantity variable with the product, but always high.

Another technique, of which the procedure according to the invention forms part, is based on the use of foucault or eddy currents. In fact, the impedance of a coil electromagnetically coupled with the product examined varies with a number of parameters linked to the latter, such as its magnetic permeability (if one is below the Curie point in the case of steel), its electric resistivity, the presence of defects and coil-product distance. This technique, like the leakage flux method, offers the advantage of making possible an estimate of the extent of the defects. However, it generally also has the disadvantage of requiring saturation magnetization of the products, in order to eliminate local variations of magnetic permeability, and then their demagnetization.

SUMMARY OF THE INVENTION

The leakage flux method and the eddy current technique just cited generally provide satisfactory sensitivity for the detection of minor defects when they are used on magnetized products. The cost of such detection, if tolerable for finished products, is often prohibitive for semifinished products. On the other hand, it is generally unnecessary to ascertain the existence of very fine defects on semifinished products.

The object of our invention is to provide an entirely automatic procedure making it possible to detect surface defects and estimate their depth or their length, applicable to nonscaled products with satisfactory sensitivity, while avoiding the obligation to magnetize and then demagnetize the product.

For that purpose, our invention concerns a procedure for inspection by eddy currents of a metal product electromagnetically coupled with a multiple number of induction coils, in relative motion with regard to the product, and grouped by pairs in bridges, the unbalance signals of which are detected, a procedure embracing the following successive operations:

samples of the unbalance voltages of said bridges are made at predetermined time intervals;

said voltages are transformed into digital signals;

the values thus obtained are stored;

the average of said values is calculated in order to obtain the base line;

the differences between said base line and each of said digital values stored are found;

said differences or their absolute values are compared with two predetermined thresholds;

windows are determined, as a function of the length of the product, so that the sum of the widths of said windows is approximately equal to the length of the product;

the sum of said absolute values of the differences between the base line and each of the digital values stored is calculated for each window;

and each of said sums is compared with a predetermined threshold.

According to a working variant of the procedure in line with our invention, applicable in the case of series of products of the same nature, the value obtained for the previously inspected product is used as base line.

The signals supplied by the measuring bridges are preferably demodulated in phase by projection on an axis chosen in advance.

Also preferably, and to assure greater sensitivity, the windows are overlapped and are of adjustable width.

Our invention likewise concerns a device for use of the procedure, consisting of:

at least one electric alternating current supply means;

at least one subassembly comprising induction coils in even number, grouped two by two in bridges connected to said power supply means, and a blocking sampler for synchronous demodulation, preceded by an amplifier stage;

and a blocking sampler associated with a digital analogue converter in order to constitute the sampling system and a computer with microprocessor type memory.

In the most complete embodiment of the device, the subassembly explained below is reproduced in a number of units equal to the number of faces of the product to be inspected.

Our invention is applicable in a particularly advantageous manner to the probing of square or rectangular billets.

As can be understood, the procedure according to our invention is based on the detection and processing of the unbalance signals from a bridge, two branches of which consist of induction coils electromagnetically coupled with the product to be inspected, those signals being a function, notably, of the presence of surface defects. In fact, even in the absence of variation of parameters influencing the impedance of the coils, particularly in a healthy zone of the product, the bridges are rarely balanced and a residual voltage can be permanently measured that is variable in the course of time. This phenomenon is caused by electronic and thermal drifts and maladjustments of the apparatus as well as by variations of grade and temperature of the product or changes in positioning of the probe. The presence of a residual voltage, on inspection of a healthy zone, is extremely disturbing, when variations of a parameter are estimated by comparison of signals supplied by the bridge to amplitude thresholds. In fact, those thresholds are generated from electric zero and, therefore, fixed in relation to the latter, while the base line, corresponding to that residual voltage, is essentially variable with test conditions and stands anywhere in relation to the thresholds. There is, consequently, a risk of not seeing certain defects and of being unable to estimate their number.

One solution to that problem consists of making the thresholds subject to the base line, but that method necessitates the use of a filtering system that is complex to make and difficult to use. Furthermore, some long defects might be confused with a variation of the base line, if the voltage they produce lasts long enough, and are, consequently, not detected. Another possibility consists of using a permanent electronic rebalancing of the bridge, but it presents the same problem: the long defects are masked, at least in part. One could, of course, in both cases estimate the length of the longest defect that can be found and impose a delay exceeding that value, but then the loss of sensitivity of the two methods becomes too great.

The solution of our invention arises out of a similar procedure, linking the thresholds to the base line, but uses a different means: actual determination of the base line from the voltages of the bridges measured in relation to electric zero, by calculation of the average value obtained by sampling. Then, depending on the application envisaged: products different from each other or series of products of the same type (same chemical composition, same magnetic permeability, same electric resistivity), one can proceed in two ways: either calculate the base line for each product or use for a given product the value of the base line obtained for the preceding product. The first method is, of course, more exact and more precise, but presents two disadvantages: all of the threshold comparison calculations are made after passage of the product and obtaining them therefore takes some time; on the other hand, it is necessary to store all the values and thus have a large-capacity memory available. In the second variant, all of the calculations are made in real time, that is, as the product passes under the probe; the waiting time after passage of the product is, consequently, short and the necessary memory capacity smaller.

DESCRIPTION OF THE DRAWING

The above and other objects, features, and advantages will be described in more detail below with reference to the attached drawing which is a schematic representation of the apparatus for carrying out the method of this invention.

SPECIFIC DESCRIPTION

The example chosen, given simply by way of illustration, concerns the low-temperature inspection of square billets. This examination can be made by the procedure according to the invention without magnetization of the billet, in the search for surface defects capable of causing rolling problems or affecting the quality of the end product, due essentially to the differential connection of the coils on each face of the billet inspected. However, in the case of products showing marked variations of magnetic permeability, it might be necessary to resort to a magnetization.

Billet 1 is inspected on each of its sides by four similar detectors. Only detector 2, placed above the upper face, has been represented, in order not to complicate the figure needlessly. That detector is identical to the one specified in French patent application No. 2,412,841, to which reference may be made for more details, if necessary. It consists here of four pairs of flat coils aa', bb', cc', dd', staggered lengthwise and crosswise to each other and lodged in a block 10 of strong dielectric material. Standard means of rolling, like runners, or of sliding, not represented, are provided in order to impart to the assembly a relative motion in relation to the billet 1 as shown by the arrow. The coils, aa', bb', cc', dd', are grouped two by two in bridges 3, the other two branches of which consist of adjustable potentiometers, connected to an alternating current supply 4, at frequency of 100 kHz in the example considered.

The unbalance voltages supplied by the four bridges of each of the sides of the billet vary with the distance of the coils from the product, with the possible presence of defects and with the variation of the magnetic characteristics of the steel. This is manifested by a displacement of the end of the vector representing in the complex plane (that is, in the amplitude-phase plane) the unbalance voltage of each bridge. It is known that the locus of that end, when just one of those parameters varies (for example, the distance between the probe and the product), is appreciably rectilinear.

Through an adequate projection of the vector in a direction parallel to that locus, the variations of impedance of the coils corresponding to that parameter can be eliminated. The principle of elimination of the influence of a disturbing parameter by such projections is set forth in French patent application No. 2,442,952, to which reference may be made, although it is a question here of a single-frequency system, while the patent application mentioned concerns a multiple-frequency system. That project is carried out here by a first blocking sampler 5, preceded by an amplifying stage 6. Blocking amplifier 5 makes a synchronous demodulation of the signal at 100 kHz, which corresponds to a projection of the vector representing the unbalance voltage on a wisely chosen axis, which can be experimentally determined by means of some tests. It was decided to regulate that projection in order to eliminate the effect of variations of distance between the probes and the billet, which are, in practice, most disturbing. In other cases, it might be necessary to eliminate another parameter. The demodulated unbalance signals are sent into a system of sampling and analogue-digital conversion with sixteen inputs, consisting of a second blocking sampler 7 associated with an analogue-digital converter 8. Blocking sampler 7 supplies, at intervals chosen in advance, making it possible to obtain sufficient precision, an analogue voltage that analogue-digital converter 8 transforms into a digital signal. In general, it is considered, taking into account the speed of the billet, that three sampling points are needed along the diameter of one coil. The beginning and the end of data acquisition are triggered by the respective passages of the head and of the end of the billet in front of a standard detector of the product's presence, e.g., of inductive or optical type, not represented.

The digital output signals Xi from analogue-digital converter 8 are introduced in a computer 9. In the present example, computer 9 is of the microprocessor type and has a memory capacity of 64 kilobytes of 16 bits and enables the probe to be made with a posteriori calculation of the average, but it would have been possible to use a computer of smaller memory capacity. Microprocessor 9 stores the Xi values and then calculates the average of those values in order to obtain the base line or OFF voltage. It then works out all of the differences:

$$Xi - OFF$$

and compares the absolute value of same with two positive thresholds $S_1$ and $S_2$. Differences higher than $S_1$ in absolute value correspond to the presence of defects and the use of a second threshold $S_2$ higher than the first makes it possible to estimate the extent of each of those defects.

For long defects, it is also important to be able to estimate the length. For that purpose, windows or zones are determined, the width of which is chosen in advance and the number of which depends on the length of the billet examined. It is possible to use either adjacent windows, the sum of the widths of which is approximately equal to the length of the billet, or, to obtain greater precision, overlapped windows. For each of the windows, the sum of the absolute values of the Xi—OFF differences is worked out and it is compared to a threshold $S_3$. Values higher than $S_3$ correspond to the presence of a long defect in the window considered and the number of windows on which that defect appears makes it possible to estimate its length.

Not all of these computing operations are immediate and it is easily conceivable that, in order not to slow down the pace of the installation where the billets arrive approximately every ten seconds, it is advantageous, in the case of probing series of identical billets, to use, from the second to the last billet, the value of the base line calculated for the previous billet. The deviations due to the equipment are, in fact, slow enough to be negligible between two successive billets. Furthermore, for billets of 12 m, for example, it is necessary, in order to assure good detection of short defects, to sample approximately 5,000 points per path and, therefore, 80,000 points all together. Taking into account the amount of data to be stored, it is then necessary to use a computer with large memory capacity.

At the end of probing of billet 1, microprocesser 9 has stored the position and type of defects (long or short) as well as the estimate of their length or size. These results can be used in different ways, by providing either marking devices which project paints of different color according to the type of defect, or mapping devices connected to the computer. The latter can, depending on criteria selected in advance, even class billet directly.

It is to be understood that each probe, such as 2, is associated with a subassembly, such as 11 (in broken lines on the figure), combining bridge 3, power supply 4, blocking sampler 5 and amplifier 6, and conversely.

In other words, the device according to our invention embraces, in its most complete embodiment, a subassembly, such as 11, connected to a probe such as 2, and the other elements, namely, blocking sampler 7, converter 8 and computer 9, which in turn are common to all probes. However, it is to be noted that power supply 4 does not necessarily form part of a subsassembly such as 11, but can be common to all probes.

Our example, of course, is not to be considered limited in scope to the example chosen, but is generally applicable and makes it possible to detect long defects and to obtain satisfactory results on scaled products.

We are claiming:

1. A method of inspecting a metal body for defects, the method comprising the steps of:
    relatively longitudinally displacing the body and a plurality of pairs of coils connected in respective bridge circuits;
    exciting the bridge circuits with alternating current;
    exciting the coils with alternating current so that eddy-current variations caused by defects in the body become impedance variations of the coils which in turn become imbalance signals in the respective bridges;
    demodulating the imbalance signals to form respective imbalance voltages;
    periodically sampling the demodulated imbalance voltages;
    storing the levels of the sampled demodulated voltages;
    averaging the sampled demodulated voltages of each bridge to produce respective base lines;
    comparing the respective stored levels of each sampled voltage with the respective base line and generating respective error signals corresponding to the differences;
    comparing each of these error signals with a relatively low threshold corresponding to the smallest defect to be detected and with a relatively high threshold;
    establishing a longitudinal succession of at least abutting zones on the body and summing error signals for each zone to obtain sums of error signals for each zone; and
    comparing each of these sums with a predetermined threshold, whereby when one of the error signals exceeds only said relatively low threshold it indicates a small defect, when one of the error signals exceeds said relatively high threshold it indicates a large defect, and when one of the sums exceeds said predetermined threshold it indicates a long defect.

2. The inspecting method defined in claim 1 wherein the imbalance signals are demodulated by projection on a predetermined axis.

3. The inspecting method defined in claim 1 wherein the zones overlap longitudinally.

4. The inspecting method defined in claim 1, further comprising the step of varying the longitudinal length of the zones.

5. The inspecting method defined in claim 1 wherein the body is generally at ambient temperature during the inspection.

6. The inspecting method defined in claim 1 wherein the body has a plurality of faces each inspected by a respective plurality of pairs of coils.

7. A method of inspecting a succession of metal bodies for defects, the method comprising the steps of:
    relatively longitudinally displacing the bodies and a plurality of pairs of coils connected in respective bridge circuits;
    exciting the bridge circuits with alternating current;
    exciting the coils with alternating current so that eddy-current variations caused by defects in the bodies become impedance variations of the coils which in turn become imbalance signals in the respective bridges;
    demodulating the imbalance signals to form respective imbalance voltages;

periodically sampling the demodulated imbalance voltages;

storing the levels of the sampled demodulated voltages;

averaging the sampled demodulated voltages of each bridge to produce respective base lines;

comparing the respective stored levels of each sampled voltage with the base line of the preceding body, with respect to the relative displacement direction, and generating respective error signals corresponding to the differences;

comparing each of these error signals with a relatively low threshold corresponding to the smallest defect to be detected and with a relatively high threshold;

establishing a longitudinal succession of at least abutting zones on the bodies and summing error signals for each zone to obtain sums of error signals for each zone; and comparing each of these sums with a predetermined threshold, whereby when one of the error signals exceeds only said relatively low threshold it indicates a small defect, when one of the error signals exceeds said relatively high threshold it indicates a large defect, and when one of the sums exceeds said predetermined threshold it indicates a long defect.

8. An apparatus for inspecting a metal body for defects, the apparatus comprising:

a plurality of bridge circuits;

respective pairs of coils connected in the bridge circuits;

means for relatively longitudinally displacing the body and the plurality of pairs of coils;

means for exciting the bridge circuits with alternating current;

means for exciting the coils with alternating current so that eddy-current variations caused by defects in the body become impedance variations of the coils which in turn become imbalance signals in the respective bridges;

means for demodulating the imbalance signals to form respective imbalance voltages;

means for periodically sampling the demodulated imbalance voltages;

means for storing the levels of the sampled demodulated voltages;

means for averaging the sampled demodulated voltages of each bridge to produce respective base lines;

means for comparing the respective stored levels of each sampled voltage with the respective base line and generating respective error signals corresponding to the differences;

means for comparing each of these error signals with a relatively low threshold corresponding to the smallest defect to be detected and with a relatively high threshold;

means for establishing a longitudinal succession of at least abutting zones on the body and summing error signals for each zone to obtain sums of error signals for each zone; and means for comparing each of these sums with a predetermined threshold, whereby when one of the error signals exceeds only said relatively low threshold it indicates a small defect, when one of the error signals exceeds said relatively high threshold it incidates a large defect, and when one of the sums exceeds said predetermined threshold it indicates a long defect.

9. The apparatus defined in claim 8 wherein the means for relatively displacing includes a block of dielectric material in which the coils are imbedded.

10. The apparatus defined in claim 8, wherein the means for comparing is a computer with microprocessor type memory.

* * * * *